(12) United States Patent
Ostgard et al.

(10) Patent No.: US 9,108,182 B2
(45) Date of Patent: Aug. 18, 2015

(54) FAST FILTERING POWDER CATALYTIC MIXTURES

(75) Inventors: Daniel Ostgard, Kleinostheim (DE); Uwe Packruhn, Frankfurt am Main (DE); Markus Göttlinger, Rodenbach (DE)

(73) Assignee: Evonik Degussa GmbH, Essen (DE)

( * ) Notice: Subject to any disclaimer, the term of this patent is extended or adjusted under 35 U.S.C. 154(b) by 425 days.

(21) Appl. No.: 12/682,080

(22) PCT Filed: Oct. 15, 2007

(86) PCT No.: PCT/EP2007/060942
§ 371 (c)(1),
(2), (4) Date: May 31, 2010

(87) PCT Pub. No.: WO2009/049662
PCT Pub. Date: Apr. 23, 2009

(65) Prior Publication Data
US 2010/0249460 A1 Sep. 30, 2010

(51) Int. Cl.
| | | |
|---|---|---|
| *B01J 23/00* | (2006.01) | |
| *B01J 23/42* | (2006.01) | |
| *B01J 23/44* | (2006.01) | |
| *B01J 21/18* | (2006.01) | |
| *B01J 23/89* | (2006.01) | |
| *B01J 35/00* | (2006.01) | |
| *B01J 37/04* | (2006.01) | |
| *C07C 209/36* | (2006.01) | |

(52) U.S. Cl.
CPC ............ *B01J 21/18* (2013.01); *B01J 23/8906* (2013.01); *B01J 35/0006* (2013.01); *B01J 37/04* (2013.01); *C07C 209/36* (2013.01)

(58) Field of Classification Search
CPC ............ B01J 23/00; B01J 23/42; B01J 23/44; B01J 23/8906
See application file for complete search history.

(56) References Cited

U.S. PATENT DOCUMENTS

| | | | |
|---|---|---|---|
| 2,619,503 A | 11/1952 | Benner et al. | |
| 2,823,235 A | 2/1958 | Graham et al. | |
| 3,127,356 A | 3/1964 | Hamilton, Jr. et al. | |
| 3,328,465 A | 6/1967 | Spiegler | |
| 3,839,011 A | 10/1974 | Larson | |
| 3,997,478 A | 12/1976 | Petro | |
| 4,153,578 A | 5/1979 | De Thomas et al. | |
| 4,182,721 A | 1/1980 | De Thomas et al. | |
| 4,224,249 A | 9/1980 | Kunz et al. | |
| 4,720,346 A | 1/1988 | Flesher et al. | |
| 4,792,626 A | 12/1988 | Becher et al. | |
| 4,978,649 A | 12/1990 | Surovikin et al. | |
| 5,051,164 A | 9/1991 | Herbst et al. | |
| 5,090,997 A | 2/1992 | Birkenstock et al. | |
| 5,238,663 A | 8/1993 | Vikari et al. | |
| 5,554,573 A | 9/1996 | Cordier et al. | |
| 6,005,143 A | 12/1999 | Machado et al. | |
| 6,309,758 B1 | 10/2001 | Schmidt | |
| 6,395,403 B2 | 5/2002 | Schmidt | |
| 6,423,872 B2 | 7/2002 | Marion | |
| 6,429,337 B1 | 8/2002 | Schmidt | |
| 8,889,910 B2 | 11/2014 | Ostgard et al. | |
| 8,889,911 B2 | 11/2014 | Ostgard et al. | |
| 2001/0027257 A1 | 10/2001 | Marion | |
| 2002/0173676 A1 | 11/2002 | Ostgard | |
| 2005/0043566 A1 | 2/2005 | Morgenstern et al. | |
| 2005/0107251 A1 | 5/2005 | Zechlin et al. | |
| 2008/0154061 A1 | 6/2008 | Ernst et al. | |
| 2008/0182745 A1* | 7/2008 | Finkelshtain et al. | ........ 502/101 |
| 2009/0264679 A1 | 10/2009 | Ostgard et al. | |
| 2010/0174116 A1 | 7/2010 | Ostgard et al. | |
| 2010/0185026 A1 | 7/2010 | Ostgard et al. | |
| 2010/0204517 A1 | 8/2010 | Ostgard et al. | |

FOREIGN PATENT DOCUMENTS

| | | |
|---|---|---|
| DE | 21 59 736 | 6/1973 |
| EP | 0 437 788 A1 | 7/1991 |
| GB | 904 117 | 8/1962 |
| GB | 1 401 673 | 7/1975 |
| JP | 62-99350 | 5/1992 |

(Continued)

OTHER PUBLICATIONS

Preliminary Amendment filed by Applicants in copending U.S. Appl. No. 12/601,815 on Nov. 24, 2009.
Preliminary Amendment filed by Applicants in copending U.S. Appl. No. 12/601,816 on Nov. 24, 2009.
Preliminary Amendment filed by Applicants in copending U.S. Appl. No. 12/601,820 on Nov. 24, 2010.
Augustine, R.L., "Unsupported Metals," Heterogeneous catalysis for the synthetic chemist, Chapter 12, pp. 229-265, Marcel Dekker, Inc., New York, NY (1996).
Chan, et al., "Materials Science and Technology," Processing of Metals and Alloys, pp. 57-110, vol. 15, VCH-Verlag Weinheim, Germany (1991).
Restriction Requirement for co-pending U.S. Appl. No. 12/601,816, mailed Jan. 27, 2012.
Response to Restriction Requirement for co-pending U.S. Appl. No. 12/601,816, filed Mar. 26, 2012.
International Search Report for PCT/EP2007/060942 filed Oct. 10, 2007.
Written Opinion of the International Searching Authority for PCT/EP2007/060942 filed Oct. 10, 2007.

(Continued)

*Primary Examiner* — Samantha Shterengarts
(74) *Attorney, Agent, or Firm* — Law Office of: Michael A. Sanzo, LLC (57) ABSTRACT

The catalytic mixture resulting of a metal powder catalyst with a solid material (referred to here as a reaction-aid) that has good filtering properties, does not interfere with the reaction, does not interfere with recycling the catalyst back into the reaction, does not interfere with the refining and recovery of the metal from the catalyst after it is spent, and will not become separated from the catalyst during the preparation of this catalytic mixture, the chemical reaction or the separation of this catalytic mixture from the reaction medium, whereas the ratio of the reaction aid to the catalyst ranges from 0.05 to 20 on a weight basis. A preferred metal powder catalyst is acetylene black supported precious metal. Preferred reaction aids are sibunit powder or activated carbon. The catalytic mixture can be used for the catalytic transformation of compounds, such as the hydrogenation of olefins, or the hydrogenation of nitro compounds.

20 Claims, 3 Drawing Sheets

(56) References Cited

FOREIGN PATENT DOCUMENTS

| | | |
|---|---|---|
| JP | 4-214807 | 8/1992 |
| JP | 55-15692 | 2/2002 |
| JP | 2002-543963 | 12/2002 |
| JP | 2004-71070 | 3/2004 |
| WO | WO 00/67903 | 11/2000 |
| WO | WO 2006/089931 A1 | 8/2006 |
| WO | WO 2006/134403 A2 | 12/2006 |
| WO | WO 2007/028411 A1 | 3/2007 |
| WO | WO 2008/145179 A1 | 12/2008 |
| WO | WO 2008/145180 A1 | 12/2008 |
| WO | WO 2008/145181 A1 | 12/2008 |

OTHER PUBLICATIONS

International Preliminary Report on Patentability for PCT/EP2007/060942 filed Oct. 10, 2007.
Neri, et al., "Kinetic Modeling of 2,4-Dinitrotoluene Hydrogenation over Pd/C," *Ind. Eng. Chem. Res.* 34:2226-2231 (1995).
Restriction Requirement for co-pending U.S. Appl. No. 12/601,820, mailed Apr. 24, 2012.
Response to Restriction Requirement for co-pending U.S. Appl. No. 12/601,820, filed May 24, 2012.
Amendment to Accompany Response to Restriction Requirement for co-pending U.S. Appl. No. 12/601,820, filed May 24, 2012.
Restriction Requirement for co-pending U.S. Appl. No. 12/601,815, mailed May 23, 2012.
Response to Restriction Requirement for co-pending U.S. Appl. No. 12/601,815, filed Jun. 16, 2012.
Amendment to Accompany Response to Restriction Requirement for co-pending U.S. Appl. No. 12/601,815, filed Jun. 16, 2012.
Lei, et al., "Preparation of novel Raney-Ni catalysts and characterization by XRD, SEM and XPS," *Applied Catalysis A: General* 214:69-76 (2001).
Response to Office Action filed Jan. 14, 2013 for co-pending U.S. Appl. No. 12/601,815.
Office Action mailed Jan. 16, 2013 for co-pending U.S. Appl. No. 12/601,816.
Office Action for co-pending U.S. Appl. No. 12/601,820, mailed Aug. 17, 2012.
Office Action for co-pending U.S. Appl. No. 12/601,816, mailed Jul. 9, 2012.
Response filed Sep. 4, 2012 for co-pending U.S. Appl. No. 12/601,816.
Office Action for co-pending U.S. Appl. No. 12/601,815, mailed Oct. 15, 2012.
Hofer, et al., "Correlation between the Catalytic Activity of Raney Nickel and its Structure," *Transactions of the Faraday Society* 60:1457-1465 (1964).
Response to Office Action filed Nov. 17, 2012 for co-pending U.S. Appl. No. 12/601,820.
English language abstract for JP 62-99350, May 8, 1992.
English language abstract for JP 4-214807, Aug. 5, 1992.
English language abstract for JP 55-15692, Feb. 2, 2002.
English language abstract for JP 2002-543963, Dec. 24, 2002.
Translation of Japanese Office Action for counterpart of copending U.S. Appl. No. 12/601,826, Sep. 28, 2012.
Translation of Japanese Office Action for counterpart of copending U.S. Appl. No. 12/601,816, Sep. 28, 2012.
International Preliminary Examination Report for PCT/EP2007/060942 (international stage of U.S. Appl. No. 12/682,080) with an international filing date of Oct. 15, 2007.
International Preliminary Examination Report for PCT/EP2007/055184 (international stage of U.S. Appl. No. 12/601,815) with an international fiing date of May 29, 2007.
International Preliminary Examination Report for PCT/EP2007/055185 (international stage of U.S. Appl. No. 12/601,816) with an international filing date of May 29, 2007.
International Preliminary Examination Report for PCT/EP2007/055186 (international stage of U.S. Appl. No. 12/601,820) with an international filing date of May 29, 2007.
English translation of Office Action in Chinese application 200780053152.6 (Chinese counterpart of U.S. Appl. No. 12/601,816) The Chinese application is national stage of an application filed May 29, 2007.
English translation of Office Action in Chinese application 200780053154.5 (Chinese counterpart of U.S. Appl. No. 12/601,820). The Chinese application is national stage of an application filed May 29, 2007.
English language abstract for JP 2004-71070, which was published on Mar. 12, 2004.
English language translation of Taiwan Office Action for co-pending U.S. Appl. No. 12/601,815. The Taiwanese application is based upon an PCT application filed on May 29, 2007.
English language abstract for German patent document DE 21 59 736, which was published on Jun. 14, 1973.
Office Action for co-pending U.S. Appl. No. 12/601,820, mailed Mar. 18, 2013.
Response to Office Action filed on Apr. 13, 2013 for co-pending U.S. Appl. No. 12/601,816, filed Apr. 13, 2013.
Office Action for copending U.S. Appl. No. 12/601,815, mailed May 23, 2013.
Response to Office Action of May 23, 2013 for U.S. Appl. No. 12/601,815, filed Aug. 23, 2013.
Advisory Action for U.S. Appl. No. 12/601,815, mailed Sep. 16, 2013.
Appeal Brief for U.S. Appl. No. 12/601,815, filed Oct. 24, 2013.
Notice of Allowance for U.S. Appl. No. 12/601,815, mailed Feb. 20, 2014.
RCE and Amendment for U.S. Appl. No. 12/601,815 filed Apr. 23, 2014.
Office Action for co-pending U.S. Appl. No. 12/601,816 mailed Sep. 10, 2013.
Response to Office Action of Sep. 10, 2013 for U.S. Appl. No. 12/601,816, filed Dec. 10, 2013.
Office Action for copending U.S. Appl. No. 12/601,816 mailed Mar. 12, 2014.
Response to Office Action of Mar. 12, 2014 for U.S. Appl. No. 12/601,816, filed Jun. 18, 2014.
Response to Office Action of Mar. 18, 2013 for U.S. Appl. No. 12/601,820, filed Jun. 18, 2013.
Advisory Action for U.S. Appl. No. 12/601,820 for U.S. Appl. No. 12/601,820 mailed Jul. 9, 2013.
Appeal Brief for U.S. Appl. No. 12/601,820 filed Oct. 24, 2013.
Notice of Allowance for U.S. Appl. No. 12/601,820 mailed Feb. 24, 2014.
RCE and Amendment for U.S. Appl. No. 12/601,820 filed Apr. 23, 2014.
Advisory Action for copending U.S. Appl. No. 12/601,816, mailed Jul. 9, 2014.
Notice of Allowance for copending U.S. Appl. No. 12/601,815, mailed Jul. 21, 2014.
Notice of Allowance for copending U.S. Appl. No. 12/601,820, mailed Jul. 21, 2014.
Appeal Brief for copending U.S. Appl. No. 12/601,816, filed Sep. 3, 2014.
Examiner's Answer for copending U.S. Appl. No. 12/601,816, mailed Dec. 2, 2014.

\* cited by examiner

*Figure 1* The Hydrogenation of DNT to TDA.

*Figure 2* The apparatus used to determine the filterability of the catalysts, supports, reaction aids and mixtures thereof.

Figure 3   The DNT pulse hydrogenation data for CE3, CE4, CE7, E1, E2, E3, E4, E6, E7 and E8.

FAST FILTERING POWDER CATALYTIC MIXTURES

CROSS REFERENCE TO RELATED APPLICATIONS

The present application is US national stage of international application PCT/EP2007/060942, which had an international filing date of Oct. 15, 2007, and which was published in English under PCT Article 21(2) on Apr. 23, 2009.

The invention of this patent concerns itself with a fast filtering powder catalytic mixture that it highly effective for chemical reactions on the basis of the amount of its catalytic metal. This invention involves forming a mixture of the metal powder catalyst with a solid material (referred to here as the reaction aid) that has excellent filtering properties, does not interfere with the reaction, does not interfere with recycling the catalyst back into the reaction, does not interfere with the refining and recovery of the metal from the catalyst after it is spent, and will not become separated from the catalyst during the preparation of this catalytic mixture, the chemical reaction or the separation of the catalytic mixture from the reaction medium.

Powder metal catalysts are used for a large number of hydrogenation, dehydrogenation, isomerization, reductive amination, reductive alkylation, oxidation, hydration and other reactions of compounds. These powdered metal catalysts are prepared by supporting small metal crystals onto a powder support such as activated carbon, carbon black, acetylene black, silica, alumina, magnesia, silica-alumina, ceria, zeolites, hydrothalcites, mixed metal oxides and other powder supports. The carbon supports have been found to be the most useful for use with the present invention and they may come from one or more sources such as, but not limited to, wood, peat, coal, saw dust, carbon containing waste materials (e.g., wood palates, agricultural waste material, plastic waste materials, polymer waste materials and others), rice husks, coconut shells, bones, lignite, petroleum based residues and sugars. Commercially available carbons which may be used in this invention include, but are not limited to, Barneby & Sutcliffe™, Darco™, Nuchar™, Columbia JXN™, Columbia LCK™, Calgon PCB™, Calcon BPL™, Westvaco™, Norit™, CECA™ and Barnaby Cheny NB™. The present invention is especially effective when used together with carbon blacks.

Carbon black is elemental carbon in a very fine particulate form that is more amorphous than graphite. It consists of planes of carbon atoms fused randomly together to form spherical particles that adhere to each other to create chainlike aggregates which in turn form agglomerates. The spherical particles range from ~10 to 500 nm and the average aggregate diameters range from 100 to 800 nm. The typical classes of carbon black are characterized by the size distribution of the spherical particles, the degree of aggregation, degree of agglomeration, the types of surface moieties and the method of production. The two main types of carbon black are produced by either the incomplete combustion method where the carbon source is oxidized in a limited amount of oxygen or the thermal decomposition method in the absence of oxygen (vide-infra). The furnace blacks are made via the incomplete combustion method and they may contain up to 15 wt % oxygen and acetylene black is made by the thermal decomposition method and is relatively oxygen free. Furnace blacks have surface areas ranging from 100 to 1500 m2/g and the surface areas of acetylene blacks range from 60 to 300 m2/g. These macro porous materials are generally believed to have "flat-surfaces" with relatively very few meso and micro pores. Furnace blacks are typically produced by burning natural gas and liquid aromatics in a furnace with a limited and controlled amount of oxygen at about ~1400° C. The ensuing cracking and polymerization of the hydrocarbons followed by their dehydrogenation lead to the formation of turbostratic carbon particles. Immediately after the reaction zone, the carbon black is quenched to 200-250° C. with a water spray to impede its further reaction with oxidizing gases such as steam and $CO_2$. Nonetheless, some oxidation does occur during the quenching step and this creates additional surface oxide groups. Acetylene black is produced in the absence of oxygen via thermal decomposition at very high temperatures (>2500° C.) and its surface is rather devoid of surface oxide groups. Thus the adsorptive properties of acetylene black are determined by its olefinic character (i.e., the ratio of its pi-to-sigma bonds). Carbon blacks conduct electrical charges and this may also play a strong role in their use as a catalyst support. Carbon blacks are also very compressible and the level of compression not only changes the physical aspects of the support, but it also effects the chemical properties such as electrical conductivity and the influence this can have on the metal crystallites supported on the carbon black where the catalysis occurs. The table below describes some of the typical carbon blacks one can use with this invention and their sources.

TABLE 1

Typical carbon blacks and their sources.

| Carbon Black Type | Chemical Process | Particle Diameter, nm | Feedstock |
|---|---|---|---|
| Lamp Black | Incomplete Combustion | 50-100 | Coal Tar Hydrocarbons |
| Channel Black | Incomplete Combustion | 10-30 | Natural Gas |
| Furnace Black | Incomplete Combustion | 10-80 | Natural Gas/ Liquid Aromatic |
| Thermal Black | Thermal Decomposition | 150-500 | Natural Gas |
| Acetylene Black | Thermal Decomposition | 35-70 | Acetylene |

These catalysts are typically prepared by suspending the powder support in a solution, adding one or more precious metal compounds to the liquid suspension with the support, fixing the metal onto the support and optionally reducing the fixed metal. The fixing agent may be added before the metal, with the metal, after the metal, during the whole process and/or combinations thereof. The fixed metal may also be oxidized before reduction, after reduction or be oxidized instead of being reduced. Another possible high temperature treatment could be in the presence of an inert gas such as nitrogen and this could be applied in various sequences and temperatures in combination with the other preparation steps mentioned above. Other gases (CO, $CO_2$, and others) and vaporized compounds (e.g., organic compounds and others) could be used as well in order to achieve the various desired effects. The suspension liquid may be aqueous, it may be organic or it could be composed of many phases and the properties of the suspension and/or its phases can be further changed at various preparation steps to modify the resulting catalyst. One such property could be the pH of the suspension at various steps of the catalyst preparation, where the addition of various bases (KOH, NaOH, $Na_2CO_3$, $NaHCO_3$ and others) and/or acids (HCl, $HNO_3$, $H_2SO_4$ and others) to a liquid suspension of the support before, after and/or during the various preparation steps can greatly impact the properties and performance of the catalyst. In the case the catalyst contains more than one metal the acid and/or base can be added before, after, during and/or in the solution containing one or more metals before addition. In the case that the different metals or metal combinations are added at different times during the various preparation steps of the catalyst, one could add the acid and/or base before, after, during and/or in the solution containing one or more metals for each of these metal additions. For further details about pH effects on catalyst preparation with aqueous phases please see F. P. Daly, W. M. Jensen and D. J. Ostgard, in Catalysis of Organic Reactions, edited by M. G. Scaros and M. L. Prunier, vol. 62 (1995) p 13-21. The catalyst could be made of one metal or more than one metal. In the case that the catalyst is made of more than one metal, all the metals could be added at once or various combinations of metals could be added during the various steps of the catalyst's preparation. The metal compounds could be salts, organic complexes, combinations thereof and others as well. The metal and/or its compound may dissolve during the preparation of the catalyst and/or the metal compound may change in-situ during preparation to produce the desired catalyst. Other suitable catalyst preparation methods for this invention include but are not limited to the use of metal evaporation, the incipient wetness spray impregnation of the various solutions used in preparing the catalyst, the wet spray impregnation of the various solutions used in preparing the catalyst, dipping the catalyst powder in various liquids and other methods as well. All commercially available powder metal catalysts can be used with the invention of this patent.

The metals used in the preparation of these catalysts can be one or more precious metals, one or more base metals, one or more alkali and alkaline metals, one or more rare earth metals or combinations of metals from one or more of these groups. This invention of this patent may also be used with Raney-type catalysts that are made by leaching out most of the Al from an alloy of Al with one or more metals that contain at least one catalytic metal and potentially modifying metals that can function as promoters, inhibitors or co-catalysts. After leaching, this activated metal powder catalyst may or may not be washed to various degrees before it is applied to the present invention.

Metal powder catalysts are typically used with liquid suspensions in tank reactors, where eventually the catalyst must be separated from the reaction mixture by sedimentation, filtration and/or other suitable methods. Other reactor types such loop reactors, cascade reactors, tube reactors and others may also take advantage of the present invention and the reaction in question may be performed batch wise, continuous, semi-continuous or by any other process method. The catalytic reaction may also involve a gas phase of one or more gases (e.g., $H_2$ for hydrogenation, $O_2$ for oxidation and $N_2$ may be used as an inert diluent) that needs to diffuse through the liquid phase to reach the solid surface of the catalyst before it can adsorb, be activated (e.g., via dissociation of $H_2$ or $O_2$) and participate in the reaction. The gas reactant may be added to the compound being transformed or it may just simply facilitate the reaction. Unfortunately some of the properties that make a catalyst very active, such as a very small support particle size and unique morphology, may also make it very difficult to filter after the reaction is performed. Hence the goal of this invention is to maintain and increase, if possible, the effectiveness of the metal in the chemical reaction while improving the filterability of the catalyst. Catalyst filtration can be performed with various screens, sintered metal discs, candle filters (e.g., Dr. M filters), membrane filters, Schenk filters, Rosemond filters and other devices for the separation of solids from liquids with or without the use of gas pressure to accelerate this separation. These methods as well as others may be used in combination with the present invention for the improved efficiency of a chemical transformation with a metal powder catalyst by allowing one to keep the best powder metal catalyst properties for the reaction while enhancing its ability to be separated from the reaction mixture at the particular time it needs to be so that the reaction can proceed smoothly and the catalyst can be easily recycled back into the system over its expected lifetime.

The present invention involves forming a mixture of the metal powder catalyst with a solid material (referred to here as a reaction aid) that has excellent filtering properties, does not interfere with the reaction, does not interfere with recycling the catalyst back into the reaction, does not interfere with the refining and recovery of the metal from the catalyst after it is spent, and will not become separated from the catalyst during the preparation of this catalytic mixture, the chemical reaction or the separation of the catalyst mixture from the reaction medium. This mixture can range from 0.05 part of reaction aid to 1 part of catalyst on a weight basis to a combination of 20 parts of reaction aid to 1 part of catalyst on a weight basis. The optimal combinations of reaction aid to catalyst on a weight basis range from 12 to 1 down to 0.5 to 1 on a weight basis. The weight ratio of reaction aid to catalyst of 5 to 1 was found to be the best for the reactions performed here.

One of the most effective materials used here was found to be a powder form of sibunit from the Institute of Hydrocarbons Processing (IHP) of the Siberian Branch of the Russian Academy of Science. Sibunit is a three dimensional matrix porous carbonaceous material that is described in U.S. Pat. No. 4,978,649, which is hereby incorporated by reference herein in its entirety. Of note are the three dimensional matrix carbonaceous materials which are obtained by introducing gaseous or vaporous carbon-containing compounds (e.g., hydrocarbons) into a mass of granules of carbonaceous material (e.g., carbon black); decomposing the carbon-containing compounds to deposit carbon on the surface of the granules; and treating the resulting material with an activator gas comprising usually of steam to provide a porous carbonaceous material in the form of a hollow body that has taken the shape of the original granule carbon material. This material can be ground to a course powder that has a surface area about ~410 m2/g and a pore volume ~0.6 cm3/g (for the pores smaller than 1500 angstroms) with ~95% of the particles being between 5 and 400 microns. Of course, other sibunit materials with different particle sizes, pore volumes and surface areas can be also used with the present invention. The sibunit powders with particle size distribution $D_{50}$ values (the value where half of the particles are greater or lower than this value) between 1000 μm and 5 μm are especially effective as reaction aids.

Other reaction aids that were found to be very effective are activated carbons. The preferred activated carbons were steam activated and/or phosphoric acid activated and had particle size distribution (PSD) $D_{50}$ values ranging from 1000 μm to 5 μm. Other activated carbons with different PSD $D_{50}$ values that were activated by other methods can also be used in the current invention.

The reaction aid may not be the best support for the catalyst in question and its function is to assist in the removal of the catalyst from the reaction suspension. In the best case, the reaction aid may also provide additional absorptive properties for the removal of catalyst poisons from the reaction mixture as the reaction proceeds. Another benefit is that it will facilitate the removal of heat during exothermic reactions by the collisions of its particles with the catalyst particles in the reaction mixture.

The reaction aid can also be specially designed to fulfill its role in the reaction medium. Specially designed activated carbons and other materials or the use of those most appropriate commercially available activated carbons and other materials for the functions of a reaction aid that meet all the above mention requirements insomuch as the catalyst remains mixed with the reaction aid during catalyst preparation, the reaction, separation of the catalytic mixture from the reaction medium and the refining of the spent catalyst for metal recovery to where none of these processes are interfered with by the reaction aid itself. During metal recovery, the activated carbon or sibunit that was used as a reaction aid can be burnt along with the spent catalyst to yield an ash rich in the catalytic metal that can be further processed. In inorganic catalytic support systems, the reaction aid will have to be as soluble as the support in the acid solution or whatever solution is used to dissolve the catalyst before the metal is recovered.

Sibunit powder is very effective as a reaction aid, in that it remains homogeneously mixed with the catalyst during catalyst preparation, the reaction, separation of the catalytic mixture from the reaction medium and the refining of the spent catalyst for metal recovery to where none of these processes are interfered with by sibunit itself. The sibunit powder can also be burnt with the spent catalyst resulting in a rapid recovery of the catalytic metal. Additional benefits of the sibunit powder is its graphitic-like conductive structure that seems to practically agglomerate with catalysts on conductive supports impregnated with metals such as the Pd+Pt+Fe on acetylene black catalysts used for the hydrogenation of aromatic nitro groups (e.g., aniline and dinitrotoluene) and the curved shape of these particles that resulted from the crushing of sibunit's original graphitic carbon hollow structures (vide-supra) which provides preferred channels in the catalyst filter cake for the reaction medium to flow through. Another benefit is that it is easier to remove more water from the catalyst in the presence of sibunit than with the catalyst alone. This will result in lower water contents meaning that one can send lower product weights when shipping the catalyst. The lower water content will also benefit catalysts that are more active in their oxidic states (e.g., the above mentioned Pd+Pt+Fe catalyst used for the hydrogenation of aromatic nitro groups) in that air can keep the catalytic metal oxidic without reduction by the support (i.e, activated carbons and other supports may be reducing agents for metals). Actually the properties of sibunit allow one to adjust the wetness of the catalytic mixture with far fewer difficulties than with the catalyst by itself, thereby improving the flexibility of this system for optimal product design and production.

The reaction aid can be added to the catalyst during any, many and/or all of the catalyst preparation steps during this procedure and this is usually, but not always, done during the last step where the catalyst preparation slurry in being homogenized by stirring before it is filtered. Another possibility would be to prepare the catalyst as it is normally done, the catalyst is then separated from the preparation slurry (via normal methods such as but not limited to sedimentation, filtration and centrifugation), the catalyst could then be optionally washed, the catalyst is then re-suspended into a slurry, the reaction aid is added to this new slurry and after it has been homogenized by stirring the new catalyst mixture is then filtered. Another possibility would be to mix the catalyst with the reaction aid in a fluidized bed of either a reactive or inert gas. In principle, any method that provides a uniform mixture between the catalyst and the reaction aid can be used to produce the invention of this patent.

One method of particular interest involves preparing the catalyst as it is normally done, allow the catalyst to settle to the bottom of the suspension's vessel after the last washing step, draw off the over-standing solution, add fresh water, add the reaction aid, stir to homogeneity and separate it from the liquid phase by a suitable method such as filtration, decantation, centrifugation, combinations of methods and other suitable means as well. One could also wash the freshly mixed catalytic mixture by allowing it to settle to the bottom of the vessel, drawing off the over-standing water, adding fresh water, stirring to homogeneity and repeat as necessary before the final catalytic mixture is separated from its last wash suspension. Instead of decantation, one could also use other suitable solid-liquid separation techniques, such as but not limited to, filtration, centrifugation and combinations of many methods for the washing of the catalyst and reaction aid mixture.

This mixture of the above mentioned reaction aid and catalyst can be used for a large range of organic transformations including, but not limited to, hydrogenation, dehydrogenation, isomerization, reductive amination, reductive alkylation, oxidation, hydration and other reactions. The moieties that can be transformed include but are not limited to: olefinic groups, acetylenic groups, nitro groups, hydroxylamines, oximes, enamines, nitrates, nitrile groups, aromatic rings, heterocyclic aromatic rings, carbonyl compounds (e.g., aldehydes and ketones), carboxylic acids, carboxlate salts, acid chlorides, imine groups, imides, esters, amides and others. The 2 main examples described here are the hydrogenation of olefinic groups such as the hydrogenation of cinnamic acid to the saturated acid and the hydrogenation of nitro groups such as with the reduction of dinitrotoluene to toluene diamine.

The hydrogenation of olefins on metal catalysts such as precious metal catalysts proceeds rapidly and the preferred support type may not be the best for filtration. Not only that, the dilution of these very active catalysts with the above mentioned reaction aids allows the reaction to progress with far fewer mass transfer limitations and the reaction's overall exotherm is considerably more controllable.

The catalytic hydrogenation of nitro groups with metal catalysts is a very demanding reaction due to the high hydrogen demand (3 hydrogen molecules per nitro group) and the very exothermic nature of this reaction. There are many types of nitro-compound hydrogenations performed in industry. One of the more commercially interesting and technically challenging is the hydrogenation of dinitrotoluene (DNT) to toluenediamine (TDA). This hydrogenation is performed with precious metal powder catalysts at temperatures ranging from room temperature to 200° C. and pressures ranging from atmospheric pressure to 200 bar. The preferred reaction conditions are within the ranges of 50° to 130° C. and 3 to 12 bar. This reaction can be performed in an excess of hydrogen or under a stoichiometric amount of hydrogen.

Figure 1:
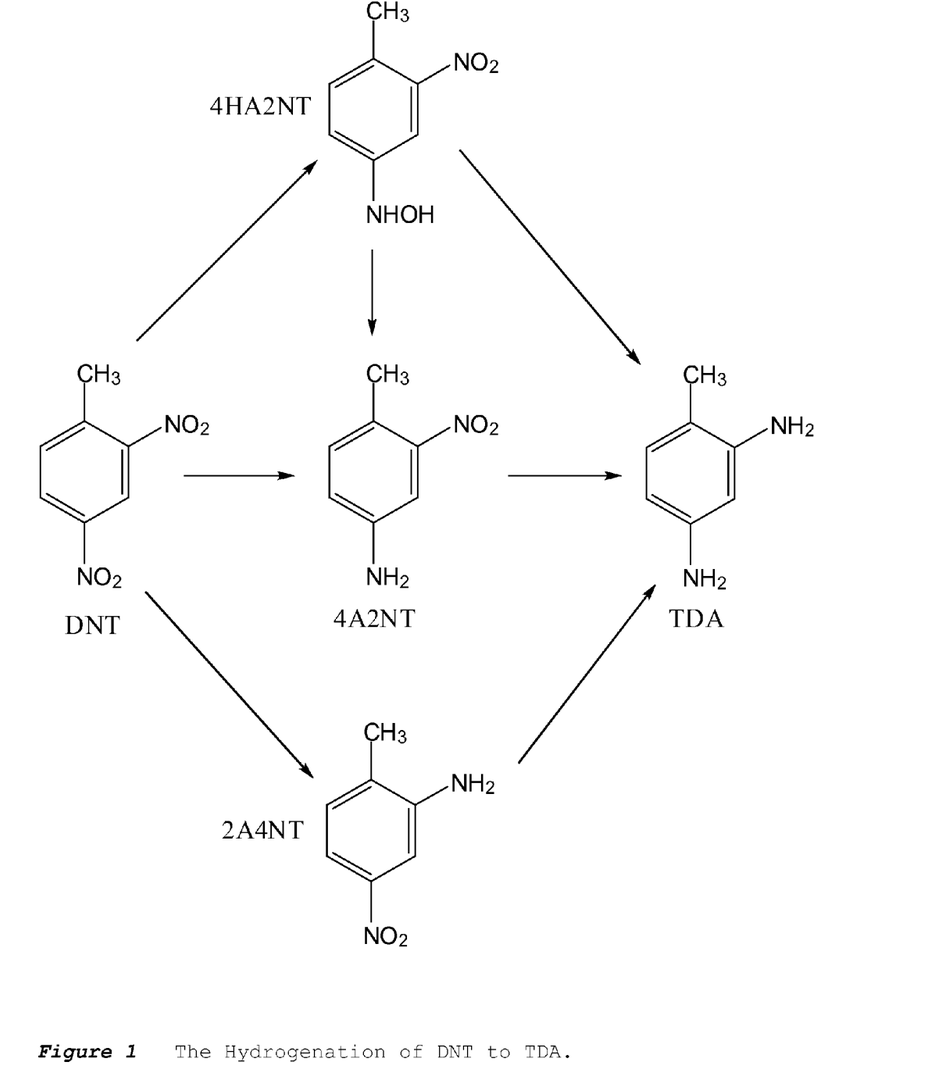
FIG. 1 illustrates the hydrogenation of DNT to TDA.

As mentioned earlier, the hydrogenation of DNT is a very exothermic and hydrogen demanding reaction that is further complicated by this reactant's strong adsorption onto the catalyst. Hence, it is easy to have a hydrogen deficient surface during this reaction and this usually leads to enhanced metal leaching and rapid catalyst deactivation due to coke formation. FIG. 1 displays the DNT hydrogenation scheme. The DNT hydrogenation data over a Pd/C catalyst from Neri et al. (please see, Neri, M. G. Musolino, S. Galvagno, Ind. Eng. Chem. Res., 34 (1995) 2226-2231) has shown that this reaction can take 3 or more parallel routes. The 2,4-DNT can be hydrogenated through an intermediate 4-hydroxyamino-2- nitrotoluene (4HA2NT) before it is converted to 4-amino-2-nitrotoluene (4A2NT) and eventually TDA. It is possible that 4HA2NT goes directly to TDA without forming 4A2NT. The 2,4-DNT can also directly form 4A2NT and then TDA without generating 2HA4NT at all.

The last route forms the 2-amino-4-nitrotoluene (2A4NT) intermediate that proceeds further to TDA. Interestingly, 2-hydroxyamino-4-nitrotoluene (2HA4NT) has not been found in any of the reaction mixtures and due to the explosive nature of hydroxylamines, the 4HA2NT should always be avoided. Regardless of the route, all of the above mentioned intermediates are very active and adsorb strongly. Thus, these intermediates and DNT can all readily yield undesired side products such as tars (e.g., dimers), light boilers (e.g., ring hydrogenated products and toluidines), products with water (e.g., methylaminocyclohexenones) and others (e.g., N-allyl-diamino toluenes) if the catalytic surface is hydrogen deficient. This can be avoided by suspending the catalyst in a hydrogen rich TDA/water mixture having the same TDA-to-water ratio as the stoichiometric product mixture produced by this hydrogenation and only pumping in enough DNT so that it is immediately hydrogenated to completion (please see U.S. Pat. No. 2,619,503) at ~6.9 bars and between 90 and 110° C. This is typically how this reaction is performed on a commercial scale, however this may not be the best testing method on a lab scale since the activity of the catalyst is dependent on the pump speed and the lifetime of the catalyst could last for days. Another laboratory testing method would be to pulse the DNT into the hydrogen rich stoichiometric TDA/water mixture (vide-supra) so that there would be only a very slight DNT access over a very limited period of time. In this way, one could measure the activity of the catalyst as a function of how much TDA per kg of precious metal that has been formed to give a catalyst deactivation profile. Based on this information, it was decided to use the above mentioned pulse test procedure at 10 bars and 120° C. for the hydrogenation of DNT over catalysts of the present invention to determine their effectiveness for this reaction.

This precious metal catalyst supported on carbonaceous materials has been optimized over the years (please see: U.S. Pat. Nos. 2,823,235, 3,127,356, and J. R. Kosak, in Catalysis of Organic Reactions, edited be R. E. Malz Jr., (1968) 31-41) and the best support was found to be acetylene black due to its highly olefinic nature. Palladium was initially chosen as the main catalytic metal due to its high activity and relatively low cost. This was improved by promoting it with a small amount of platinum, however this catalyst was too active and yielded unwanted side products via reactions like ring hydrogenation. The selectivity of this catalyst was then corrected by the addition of iron oxide that impeded the undesired reactions. Iron has also been proven to be a promoter for the hydrogenation of aliphatic nitro compounds [please see: E. Auer, M. Berweiler, M. Gross, J. Pietsch, D. J. Ostgard, P. Panster, in Catalysis of Organic Reactions, edited by M. E. Ford, vol. 82 (2001)293-300] as well as for nitro-aromatics, where it was additionally useful for avoiding ring hydrogenation. One of the catalysts from this optimization work has a 0.75 wt. % Pd+0.083 wt. % Pt+0.853 wt. % Fe metal combination supported on acetylene black that not only exhibited high activity, but also high selectivity. This catalyst was made by precipitating 4.5 wt. % Pd+0.5 wt. % Pt+5 wt. % Fe onto the acetylene black support followed by the dilution of the catalyst with fresh acetylene black at the ratio of 5 parts of acetylene black to 1 part of the 4.5 wt. % Pd+0.5 wt. % Pt+5 wt. % Fe on acetylene black catalyst to result in the overall metal loading of 0.75 wt. % Pd+0.083 wt. % Pt+0.853 wt. % Fe.

While acetylene black is the best support for the highest hydrogenation rate, its above mentioned physical and chemical properties make if very difficult to separate from the reaction mixture by filtration or any other method even if one mixes fresh acetylene black at a ratio of 5-to-1 with the catalyst. Hence the choice to use an acetylene black supported catalyst means that one favors a fast and selective hydrogenation over fast filtration.

Activated carbon supported catalysts have also been found to be useful for the hydrogenation of DNT to TDA [please see, Neri, M. G. Musolino, S. Galvagno, Ind. Eng. Chem. Res., 34 (1995) 2226-2231] and while the activated carbon supported catalysts filter much faster than the acetylene black supported ones, these catalysts are far less active and less selective. Activated carbons have far more meso and micro pores than acetylene black. If the metal crystals deposit in these smaller pores, the resulting activated carbon supported catalyst will have more problems with mass transfer limitations into and out of the pores and in this case, the hydrogenation rate can quickly become dependent on the diffusion rate of hydrogen into these smaller pores for these metal crystals. Not only does that make the metal crystals in these pores less active, they are also more likely to form tars due to the strong adsorption strength of DNT under hydrogen deficient conditions resulting in faster deactivation rates and lower reaction selectivity. The resulting TDA and potential side products can also readsorb on other metal crystals as they diffuse out of the carbon's pore system and that will increase the chances of even more secondary reactions leading to even lower reaction selectivity. Moreover, activated carbons are not conductive and they cannot take advantage of this mild metal-to-support interaction between the active site on the catalytic metal and the electronic structure of the support, as is the case with acetylene black. Hence the choice to use an activated carbon supported catalyst means that one favors a fast filtration over faster hydrogenation rates and better product selectivity.

Thus the choice of catalyst determines the bottleneck of the process and it wasn't until the present invention that one could have high activity with high selectivity and fast filtration. The catalyst systems that worked the best for the hydrogenation of DNT were the different acetylene black supported 4.5 wt. % Pd+0.5 wt. % Pt+5 wt. % Fe catalysts that were diluted 5-to-1 with the sibunit powder. It was also found to be rather useful to wash the catalyst before it was mixed with the reaction aid.

Another preferred embodiment of this invention was the 5-to-1 dilution of an 4.5 wt. % Pd+0.5 wt. % Pt+5 wt. % Fe on acetylene black catalyst with a steam activated carbon made from wood and comprising of needle shaped particles that pack to form catalyst beds with preferred channels for the liquid reaction medium to flow through. Other activated carbons from other sources, carbons activated by different methods, carbons activated by more than one method and carbons that are not even activated at all along with carbons having different morphologies can also be preferred reaction aids if they fulfill the reaction aid requirements described in this patent.

The hydrogenation of nitro-compounds can take place in the vapor, slurry, trickle, aerosol and/or liquid phase. The reaction could be performed as a batch process or it could be performed as a continuous process. The continuous processes may involve, but they are not limited to, a type of circulation process. This invention also includes a continuous process where the nitro-compound is added at a rate that is the same or slower than the rate of hydrogenation, so that the concentration of the nitro-compound is kept to a very low level. The feeding rate of the nitro-compound may be so low that the level of the nitro-compound is 1000 ppm or lower. Of course, this reaction can be performed at a controlled excess of DNT by balancing the rate of DNT addition to catalyst's hydrogenation rate. This invention also includes the use of the previously mentioned catalyst of this invention in a continuous process that utilizes a second hydrogenation reactor (or more) to hydrogenate any nitro-compounds and/or intermediates that were remaining from the hydrogenation in the first hydrogenation reactor.

The nitro-compound hydrogenation of this invention may take place in the presence of the neat nitro-compound, at high concentrations of the reactant, at very low concentrations of the reactant and/or in the presence of the product mixture that would be acting like a solvent. This hydrogenation may also take place in the presence of practically only the desired amine or under lower water contents than what is stoichiometrically produced if the water is removed by a satisfactory method (e.g., distillation) during the reaction. The nitro-compound hydrogenation of this invention may take place in the presence of a solvent. The reactor type could be, but is not limited to, a stirred tank reactor, a continuous stirred tank reactor, a loop reactor or a tube reactor. This nitro-compound hydrogenation may occur between atmospheric pressure and 200 bars of hydrogen and the temperature can range from ~10° C. to 210° C.

This invention encompasses the preparation and the use of a catalytic mixture comprising of a reactive and selective catalyst along with a reaction aid for the effective (on a metal basis) catalytic transformation of compounds into their products followed by the rapid separation of this mixture from the reaction medium as facilitated by the reaction aid. The reaction aid has to have good filtration properties, does not interfere with the reaction, does not interfere with recycling the catalyst back into the reaction, does not interfere with the refining and recovery of the metal from the catalyst after it is spent, and will not become separated from the catalyst during the preparation of this catalytic mixture, the chemical reaction, separation of the catalytic mixture from the reaction medium and during the refining and recovery of metal from the spent catalytic mixture. This invention also includes the above mentioned catalytic mixture as a composition of matter.

BRIEF DESCRIPTION OF THE DRAWINGS

FIG. 1.

FIG. 2.

FIG. 3.

APPLICATION EXAMPLE 1

The pulse hydrogenation of dinitrotoluene (DNT) to toluenediamine (TDA).

DNT is typically hydrogenated in an industrial setting via a continuous mode, where the DNT feed rate is slow enough to keep its concentration low enough so that it doesn't poison the catalyst or become a safety hazard. This means that the hydrogenation rate will be dependent on the DNT feed rate. The goal of our pulse hydrogenation method was to keep the DNT concentration low enough so that it would be comparable to the industrial setting while measuring the activity of the catalyst. We were able to do so by pulsing in the DNT feed at a rate that was slightly faster than the rate of hydrogenation so that we could measure catalyst activity while keeping the time of the slight excess of DNT to a minimum.

The pulse hydrogenation method was started by placing enough catalyst in the reactor so that exactly 3 milligrams of precious metal sum total are present along with 101 grams of TDA and 59 grams of water (the reaction's stoichiometric TDA-to-water ratio) in the 500 ml autoclave. The autoclave was then closed, purged with nitrogen 3 times, purged 3 times with hydrogen and heated to the reaction temperature of 120° C. over a period of 20 minutes while the reactor was stirring at 300 rpm and kept under 5 bar hydrogen. Once the autoclave reached 120° C., the hydrogen pressure was adjusted to 10 bar hydrogen and the stirring rate was increased to 1700 rpm. The reaction was then started by pulsing 4 milliliters of molten DNT into the reactor over 30 seconds with an HPLC pump. The HPLC pump head, the DNT reservoir and all the stainless tubing used for the transport of DNT was kept at 95° C. to keep the DNT molten. A Büchi hydrogen press flow controller (bpc 9901) was used to monitor the hydrogen consumption and once the reaction stopped to consume hydrogen, another pulse of DNT was introduced at the same feed rate. This procedure was continued up to a maximum of 45 pulses had been introduced. The data from these hydrogenations can be seen in FIG. 3 and in data tables 4 to 14.

APPLICATION EXAMPLE 2

The batch hydrogenation of cinnamic acid.

The low pressure hydrogenation of cinnamic acid was carried out over 200 milligrams of catalyst slurried into 40 ml of ethanol and added to 80 ml of a 0.844 M cinnamic acid ethanolic solution at 25° C. and atmospheric pressure in a baffled glass reactor outfitted with a hallow shaft bubble inducing stirrer. The reaction began as the stirrer was started and spun at 2000 rpm during the reaction. The total hydrogenation uptake between the third and eighth minutes of the reaction was divided by 5 and then divided by 200 to calculate the cinnamic acid activity value in units of ml of hydrogen per minute per mg of catalyst. The cinnamic acid hydrogenation activity was also calculated on the mg of precious metal basis to facilitate the comparison of the different catalysts. The results of these hydrogenations are listed in table 1.

TABLE 2

The cinnamic acid hydrogenation data.

| Catalyst | Cinnamic Acid Activity ml $H_2$/min/ mg catalyst | Cinnamic Acid Activity ml $H_2$/min/mg precious metal |
| --- | --- | --- |
| Comparative Example 3 | 67 | 8043 |
| Comparative Example 4 | 222 | 4440 |
| Comparative Example 6 | 196 | 3920 |
| Comparative Example 8 | 34 | 1700 |
| Example 1 | 86 | 10324 |
| Example 2 | 96 | 11525 |
| Example 4 | 76 | 9124 |

APPLICATION EXAMPLE 3

Determining the Filterability of the Catalyst

Figure 2:
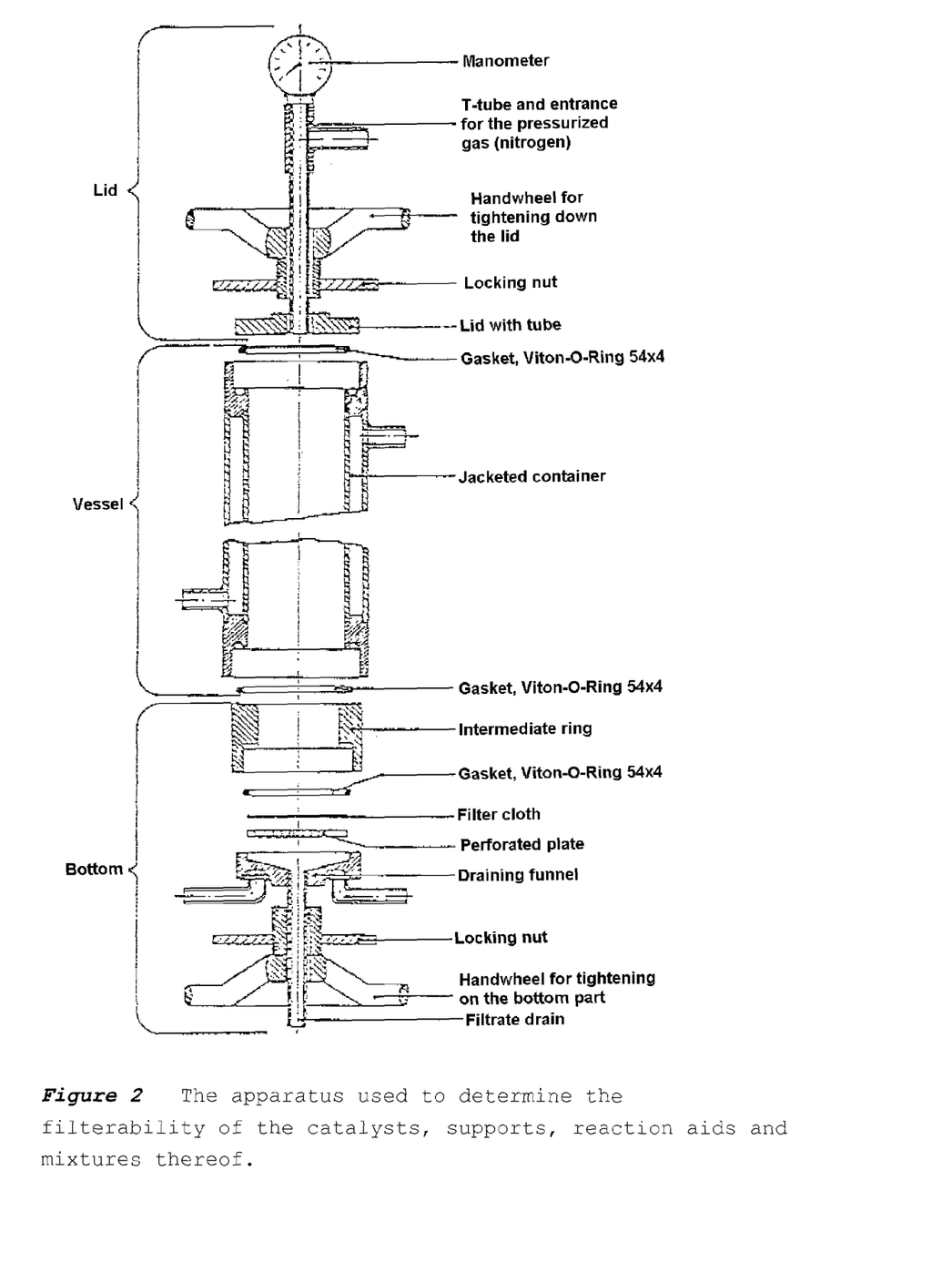
FIG. 2 illustrates an apparatus used to determine the filterability of catalysts, supports, reaction aids and mixtures thereof.

The apparatus in FIG. 2 is used for determining the filterability of the catalyst. The lid of this apparatus has a t-tube outfitted with an inlet for a pressurized gas (e.g., nitrogen or air) and a monometer so that the pressure can be monitored and controlled. The lid can be attached and tightened onto the main vessel with a hand-wheel and a locking nut, and this is made airtight by the use of a viton-o-ring gasket. The main vessel consists of a jacketed container (a stainless steel cylinder) that can be connected in an airtight fashion with the help of a viton-o-ring to an intermediate ring (or cylinder) that goes over another viton-o-ring, a filter cloth, a perforated plate and finally the draining funnel that can be locked into place with a hand-wheel and a locking nut. At the bottom of the draining funnel is a drainage tube that is directed to an empty beaker. Before carrying out each test, a blank run is performed with 400 ml of deionised water to check if the filter cloth is free of support materials, reaction aids and catalyst particles from the previous tests. The blank test is performed by placing a stopper in the drainage tube coming from the draining funnel, 400 ml of deionised water is poured into the jacketed container, the filtration unit is then closed by putting on the lid and tightening it, the plug is then removed from the drainage tube, the device is pressurized with a gas from the T-tube on the lid to exactly 1 bar and the stopwatch is started simultaneously. The time it takes for all of the water to be pressed out is measured in seconds and the stopwatch is stopped after all the liquid is pushed out and at the appearance of the first gas bubbles. If the blank test is quicker than 4 seconds, then the filter cloth is still O.K. If not, the filter cloth will have to be replaced. The test is performed by placing a stopper in the drainage tube followed by suspending 10 grams of the catalyst, support, reaction aid or mixtures thereof into 390 ml of deionised water. Any agglomerates that are present should be broken up by swirling the beaker of the suspension. The suspension is then stirred 15 seconds with a Krups 3 mix 4004 high speed mixing rod on level 3 before it is immediately poured into the filtration unit and the beaker is then rinsed out into the filtration unit with 10 ml of deionised water. In a very quick fashion, The lid is tightened in place, the stopper is removed from the drainage tube, the gas pressured is adjusted to exactly 1 bar and the stopwatch in simultaneously started. The time runs until all of the water comes out of the drainage tube and the first gas bubbles appear. After the measurement the filtration apparatus is taken apart and cleaned thoroughly with water. The filter cloth can be cleaned by forcing water back up the drainage tube and through the filter cloth before the next blank run is performed. Each catalyst, support, reaction aid or mixture thereof is measured 3 times and the average values of these tests are listed in table 3 for the above mentioned materials measured here.

TABLE 3

The filterability of the catalysts, supports, reaction aids and mixtures thereof.

| Catalyst or Support | Filtration Time, in minutes (m) and seconds (s) |
| --- | --- |
| Comparative Example 1 | 5 m 15 s |
| Comparative Example 2 | 0 m 41 s |
| Comparative Example 3 | 4 m 30 s |
| Comparative Example 4 | >8 m |
| Comparative Example 5 | 4 m 28 s |
| Comparative Example 6 | >8 m |
| Comparative Example 8 | 0 m 35 s |
| Example 1 | 2 m 03 s |
| Example 2 | 2 m 15 s |
| Example 3 | 2 m 24 s |
| Example 5 | 2 m 41 s |
| Example 6 | 3 m 08 s |
| Example 9 | 3 m 72 s |
| Example 10 | 2 m 18 s |
| Example 11 | 0 m 38 s |

COMPARATIVE EXAMPLE 1

A commercially available 50% compressed acetylene black used as a support for the catalysts in this patent contained less than 1 wt. % water and had a filtration time of 5 minutes and 15 seconds (please see Application example 3 and table 3).

COMPARATIVE EXAMPLE 2

A sibunit powder (vide-supra) with 95% of its particles between 5 and 400 microns, a BET surface area of ~410 $m^2$/gram and a pore volume of 0.6 $cm^3$/gram (for the pores smaller than 1500 angstroms) was used as a support and a reaction aid for the catalysts in this patent. This material contained less than 1 wt. % water and had the filtration time of 0 minutes and 41 seconds (please see Application example 3 and table 3).

COMPARATIVE EXAMPLE 3

One part of a commercially available 4.5 wt. % Pd+0.5 wt. % Pt+5.0 wt. % Fe on a 50% compressed acetylene black catalyst made by Degussa's proprietary technology was mixed with 5 parts of a fresh 50% compressed acetylene black on a weight basis in an aqueous suspension, stirred to homogeneity, and filtered. The resulting mixture had the final metal loading of 0.75 wt. % Pd+0.083 wt. % Pt+0.83 wt. % Fe, contained 74.2 wt. % water and had a filtration time of 4 minutes and 30 seconds (please see Application example 3). This catalytic mixture had a cinnamic acid hydrogenation activity of 8043 ml $H_2$ per minute per milligram of precious metal (please see application example 2) and it was also tested for the pulse hydrogenation of DNT to TDA as according to application example 1. The results for the DNT hydrogenation test can be seen in table 4 and FIG. 3. The maximum DNT hydrogenation activity during this test was 429 ml $H_2$/min/mg of precious metal and the final activity was 236 ml $H_2$/min/mg of precious metal at the yield of 39.9 MT of TDA per kg of precious metal resulting in a deactivation rate of 45% over this range.

TABLE 4

The dinitrotoluene hydrogenation data for comparative example 3.

| Metric Tons TDA yielded per kilogram of precious metal | Hydrogenation Activity in ml $H_2$ per minute per milligram of precious metal |
| --- | --- |
| 0.6 | 235 |
| 1.3 | 277 |
| 2.1 | 316 |
| 3.1 | 400 |
| 4.1 | 400 |
| 5.2 | 429 |
| 6.3 | 420 |
| 7.4 | 427 |
| 8.6 | 424 |
| 9.7 | 402 |
| 10.8 | 417 |
| 11.9 | 407 |
| 13.0 | 383 |
| 14.1 | 393 |
| 15.2 | 374 |
| 16.4 | 369 |
| 17.5 | 359 |
| 18.6 | 351 |
| 19.7 | 320 |
| 20.8 | 341 |
| 22.0 | 343 |

TABLE 4-continued

The dinitrotoluene hydrogenation data for comparative example 3.

| Metric Tons TDA yielded per kilogram of precious metal | Hydrogenation Activity in ml H$_2$ per minute per milligram of precious metal |
|---|---|
| 23.1 | 332 |
| 24.2 | 326 |
| 25.4 | 315 |
| 26.5 | 310 |
| 27.6 | 300 |
| 28.7 | 283 |
| 29.8 | 290 |
| 30.9 | 270 |
| 32.1 | 271 |
| 33.2 | 266 |
| 34.3 | 263 |
| 35.4 | 255 |
| 36.5 | 266 |
| 37.7 | 246 |
| 38.8 | 244 |
| 39.9 | 236 |

COMPARATIVE EXAMPLE 4

A commercially available 4.5 wt. % Pd+0.5 wt. % Pt+5.0 wt. % Fe on a 50% compressed acetylene black catalyst made by Degussa's proprietary technology contained 81.1 wt. % water and had a filtration time longer than 8 minutes (please see Application example 3). This catalyst had a cinnamic acid hydrogenation activity of 4440 ml H$_2$ per min per milligram of precious metal (please see application example 2) and it was also tested for the pulse hydrogenation of DNT to TDA as according to application example 1. The results for the DNT hydrogenation test can be seen in table 5 and FIG. 3. The maximum DNT hydrogenation activity during this test was 367 ml H$_2$/min/mg of precious metal and the final activity was 219 ml H$_2$/min/mg of precious metal at the yield of 40 MT of TDA per kg of precious metal resulting in a deactivation rate of 40.3% over this range.

TABLE 5

The dinitrotoluene hydrogenation data for comparative example 4.

| Metric Tons TDA yielded per kilogram of precious metal | Hydrogenation Activity in ml H$_2$ per minute per milligram of precious metal |
|---|---|
| 0.7 | 207 |
| 1.4 | 238 |
| 2.1 | 294 |
| 3.2 | 320 |
| 4.3 | 347 |
| 5.4 | 367 |
| 6.5 | 354 |
| 7.6 | 336 |
| 8.7 | 365 |
| 9.9 | 356 |
| 11.0 | 348 |
| 12.1 | 338 |
| 13.2 | 360 |
| 14.4 | 343 |
| 15.5 | 336 |
| 16.6 | 321 |
| 17.7 | 332 |
| 18.8 | 330 |
| 20.0 | 332 |
| 21.1 | 314 |
| 22.2 | 298 |
| 23.3 | 289 |
| 24.4 | 290 |
| 25.5 | 288 |
| 26.7 | 281 |
| 27.7 | 270 |
| 28.9 | 278 |
| 30.0 | 264 |
| 31.1 | 253 |
| 32.2 | 258 |
| 33.3 | 254 |
| 34.4 | 239 |
| 35.5 | 252 |
| 36.6 | 233 |
| 37.8 | 237 |
| 38.9 | 219 |
| 40.0 | 219 |

COMPARATIVE EXAMPLE 5

One part of a commercially available 4.5 wt. % Pd+0.5 wt. % Pt+5.0 wt. % Fe on a 50% compressed acetylene black catalyst made by Degussa's proprietary technology was mixed with 5 parts of a fresh 50% compressed acetylene black on a weight basis in an aqueous suspension, stirred to homogeneity, and filtered. The resulting mixture had the final metal loading of 0.75 wt. % Pd+0.083 wt. % Pt+0.83 wt. % Fe, contained 77.8 wt. % water and had a filtration time of 4 minutes and 28 seconds (please see Application example 3).

COMPARATIVE EXAMPLE 6

A commercially available 4.5 wt. % Pd+0.5 wt. % Pt+5.0 wt. % Fe on a 100% compressed acetylene black catalyst made by Degussa's proprietary technology contained 78 wt. % water and had a filtration time longer than 8 minutes (please see Application example 3). This catalyst had a cinnamic hydrogenation activity of 3920 ml H$_2$ per min per milligram of precious metal (please see application example 2).

COMPARATIVE EXAMPLE 7

A commercially available 4 wt. % Pd+1.0 wt. % Pt+1.0 wt. % Fe on an activated carbon catalyst made by Degussa's proprietary technology was tested for the pulse hydrogenation of DNT to TDA as according to application example 1. The results for the DNT hydrogenation test can be seen in table 6 and FIG. 3. The maximum DNT hydrogenation activity during this test was 216 ml H$_2$/min/mg of precious metal and the final activity was 173 ml H$_2$/min/mg of precious metal at the yield of 24.28 MT of TDA per kg of precious metal resulting in a deactivation rate of 19.9% over this range.

TABLE 6

The dinitrotoluene hydrogenation data for comparative example 7.

| Metric Tons TDA yielded per kilogram of precious metal | Hydrogenation Activity in ml H$_2$ per minute per milligram of precious metal |
|---|---|
| 0.56 | 158 |
| 1.20 | 167 |

TABLE 6-continued

The dinitrotoluene hydrogenation data for comparative example 7.

| Metric Tons TDA yielded per kilogram of precious metal | Hydrogenation Activity in ml $H_2$ per minute per milligram of precious metal |
|---|---|
| 1.87 | 174 |
| 2.50 | 204 |
| 3.21 | 209 |
| 3.90 | 199 |
| 4.61 | 198 |
| 5.37 | 191 |
| 6.01 | 203 |
| 6.72 | 216 |
| 7.39 | 207 |
| 8.09 | 216 |
| 8.82 | 209 |
| 9.53 | 212 |
| 10.25 | 203 |
| 10.96 | 213 |
| 11.69 | 200 |
| 12.38 | 207 |
| 13.09 | 207 |
| 13.79 | 196 |
| 14.48 | 190 |
| 15.21 | 193 |
| 15.94 | 188 |
| 16.61 | 197 |
| 17.33 | 194 |
| 18.00 | 188 |
| 18.62 | 186 |
| 19.33 | 182 |
| 20.04 | 187 |
| 20.75 | 192 |
| 21.47 | 190 |
| 22.14 | 182 |
| 22.85 | 177 |
| 23.56 | 185 |
| 24.28 | 173 |

COMPARATIVE EXAMPLE 8

A commercially available catalyst consisting of 1.8 wt. % Pd+0.2 wt. % Pt+2.0 wt. % Fe on sibunit powder (this powder sibunit is described in comparative example 2) that was made by Degussa's proprietary technology contained 27.3 wt. % water and had a filtration time of 0 minutes and 35 seconds (please see Application example 3). This catalyst had a cinnamic acid hydrogenation activity of 1700 ml $H_2$ per min per milligram of precious metal (please see application example 2) and it was also tested for the pulse hydrogenation of DNT to TDA as according to application example 1. The activity results for the DNT hydrogenation test were so low that they could not be reliably measured and the experiment had to be stopped quite early after its start so as to avoid the unsafe build up of nitro bodies in the reaction medium. One can safely assume that this catalyst is relatively inactive for the hydrogenation of DNT.

EXAMPLE 1

One part of a commercially available 4.5 wt. % Pd+0.5 wt. % Pt+5.0 wt. % Fe on a 50% compressed acetylene black catalyst made by Degussa's proprietary technology was washed very well with deionised water and after washing, it was mixed with 5 parts of sibunit powder (this sibunit powder was described in comparative example 2) on a weight basis in an aqueous suspension, stirred to homogeneity, and filtered. The resulting mixture had the final metal loading of 0.75 wt. % Pd+0.083 wt. % Pt+0.83 wt. % Fe, contained 0.9 wt. % water and had a filtration time of 2 minutes and 03 seconds (please see Application example 3). This catalytic mixture had a cinnamic acid hydrogenation activity of 10324 ml $H_2$ per min per milligram of precious metal (please see application example 2) and it was also tested for the pulse hydrogenation of DNT to TDA as according to application example 1. The results for the DNT hydrogenation test can be seen in table 7 and FIG. 3. The maximum DNT hydrogenation activity during this test was 632 ml $H_2$/min/mg of precious metal and the final activity was 510 ml $H_2$/min/mg of precious metal at the yield of 40.1 MT of TDA per kg of precious metal resulting in a deactivation rate of 19.3% over this range.

TABLE 7

The dinitrotoluene hydrogenation data for example 1.

| Metric Tons TDA yielded per kilogram of precious metal | Hydrogenation Activity in ml $H_2$ per minute per milligram of precious metal |
|---|---|
| 0.8 | 397 |
| 1.7 | 406 |
| 2.7 | 420 |
| 3.8 | 511 |
| 4.8 | 490 |
| 6.0 | 500 |
| 7.1 | 556 |
| 8.3 | 554 |
| 9.5 | 576 |
| 10.7 | 563 |
| 11.9 | 547 |
| 13.1 | 567 |
| 14.3 | 603 |
| 15.5 | 574 |
| 16.7 | 600 |
| 17.9 | 563 |
| 19.0 | 602 |
| 20.2 | 632 |
| 21.4 | 602 |
| 22.5 | 632 |
| 23.7 | 612 |
| 24.9 | 576 |
| 26.0 | 622 |
| 27.2 | 592 |
| 28.4 | 548 |
| 29.6 | 628 |
| 30.8 | 574 |
| 31.9 | 559 |
| 33.1 | 583 |
| 34.3 | 552 |
| 35.5 | 613 |
| 36.6 | 565 |
| 37.8 | 507 |
| 39.0 | 578 |
| 40.1 | 510 |

EXAMPLE 2

During the last steps of the preparation of a 4.5 wt. % Pd+0.5 wt. % Pt+5.0 wt. % Fe catalyst on a 100% compressed acetylene black made by Degussa's proprietary technology, sibunit powder (this sibunit powder was described in comparative example 2) was added to the aqueous suspension of the catalyst in the ratio of 5 parts sibunit powder to 1 part catalyst on a weight basis. This mixture was stirred to homogeneity, filtered and then washed with deionised water. The resulting catalytic mixture had the final metal loading of 0.75 wt. % Pd+0.083 wt. % Pt+0.83 wt. % Fe, contained 29.7 wt. % water and had a filtration time of 2 minutes and 15 seconds (please see Application example 3). This catalytic mixture had a cinnamic acid hydrogenation activity of 11525 ml $H_2$ per minute per milligram of precious metal (please see application example 2) and it was also tested for the pulse hydrogenation of DNT to TDA as according to application example 1. The results for the DNT hydrogenation test can be seen in table 8 and FIG. 3. The maximum DNT hydrogenation activity during this test was 418 ml $H_2$/min/mg of precious metal and the final activity was 297 ml $H_2$/min/mg of precious metal at the yield of 39.9 MT of TDA per kg of precious metal resulting in a deactivation rate of 28.9% over this range.

TABLE 8

The dinitrotoluene hydrogenation data for example 2.

| Metric Tons TDA yielded per kilogram of precious metal | Hydrogenation Activity in ml $H_2$ per minute per milligram of precious metal |
|---|---|
| 0.79 | 212 |
| 0.82 | 289 |
| 1.72 | 314 |
| 2.48 | 327 |
| 3.33 | 358 |
| 4.17 | 373 |
| 4.69 | 368 |
| 5.78 | 365 |
| 6.90 | 357 |
| 7.68 | 398 |
| 9.92 | 396 |
| 11.04 | 383 |
| 12.22 | 392 |
| 13.37 | 418 |
| 14.55 | 409 |
| 15.67 | 407 |
| 16.85 | 400 |
| 17.97 | 407 |
| 19.12 | 411 |
| 20.27 | 385 |
| 21.45 | 365 |
| 22.60 | 387 |
| 23.75 | 374 |
| 24.93 | 367 |
| 26.08 | 368 |
| 27.22 | 350 |
| 28.40 | 354 |
| 29.55 | 341 |
| 30.61 | 319 |
| 31.76 | 318 |
| 32.91 | 339 |
| 34.06 | 329 |
| 35.24 | 327 |
| 36.42 | 308 |
| 37.57 | 300 |
| 38.72 | 294 |
| 39.90 | 297 |

EXAMPLE 3

During the last steps of the preparation of a 4.5 wt. % Pd+0.5 wt. % Pt+5.0 wt. % Fe catalyst on a 100% compressed acetylene black made by Degussa's proprietary technology, sibunit powder (this sibunit powder was described in comparative example 2) was added in the ratio of 5 parts sibunit powder to 1 part catalyst on a weight basis to an aqueous suspension of the catalyst. This mixture was stirred to homogeneity, filtered and then washed with deionised water. The resulting catalytic mixture had the final metal loading of 0.75 wt. % Pd+0.083 wt. % Pt+0.83 wt. % Fe, contained 35.7 wt. % water and had a filtration time of 2 minutes and 24 seconds (please see Application example 3). This catalytic mixture was also tested for the pulse hydrogenation of DNT to TDA as according to application example 1. The results for the DNT hydrogenation test can be seen in table 9 and FIG. 3.

The maximum DNT hydrogenation activity during this test was 407 ml $H_2$/min/mg of precious metal and the final activity was 295 ml $H_2$/min/mg of precious metal at the yield of 38.7 MT of TDA per kg of precious metal resulting in a deactivation rate of 27.5% over this range.

TABLE 9

The dinitrotoluene hydrogenation data for example 3.

| Metric Tons TDA yielded per kilogram of precious metal | Hydrogenation Activity in ml $H_2$ per minute per milligram of precious metal |
|---|---|
| 1.1 | 340 |
| 2.1 | 321 |
| 3.2 | 348 |
| 4.3 | 341 |
| 5.4 | 359 |
| 6.5 | 361 |
| 7.6 | 365 |
| 8.7 | 370 |
| 9.7 | 357 |
| 10.9 | 378 |
| 11.9 | 368 |
| 13.0 | 352 |
| 14.2 | 365 |
| 15.2 | 407 |
| 16.3 | 395 |
| 17.5 | 376 |
| 18.6 | 395 |
| 19.7 | 381 |
| 20.8 | 404 |
| 21.9 | 387 |
| 23.1 | 375 |
| 24.2 | 375 |
| 25.3 | 402 |
| 26.4 | 393 |
| 27.5 | 385 |
| 28.6 | 350 |
| 29.8 | 371 |
| 30.9 | 354 |
| 32.0 | 356 |
| 33.1 | 335 |
| 34.2 | 317 |
| 35.3 | 336 |
| 36.5 | 316 |
| 37.6 | 307 |
| 38.7 | 295 |

EXAMPLE 4

One part of a commercially available 4.5 wt. % Pd+0.5 wt. % Pt+5.0 wt. % Fe on a 50% compressed acetylene black catalyst made by Degussa's proprietary technology was diluted with 5 parts of sibunit powder (this sibunit powder was described in comparative example 2) on a weight basis in an aqueous suspension that was stirred to homogeneity and filtered. The resulting mixture had the final metal loading of 0.75 wt. % Pd+0.083 wt. % Pt+0.83 wt. % Fe and had a cinnamic acid hydrogenation activity of 9124 ml $H_2$ per min per milligram of precious metal (please see application example 2). This catalyst was also tested for the pulse hydrogenation of DNT to TDA as according to application example 1. The results for the DNT hydrogenation test can be seen in table 10 and FIG. 3. The maximum DNT hydrogenation activity during this test was 487 ml $H_2$/min/mg of precious metal and the final activity was 327 ml $H_2$/min/mg of precious metal at the yield of 38.99 MT of TDA per kg of precious metal resulting in a deactivation rate of 32.9% over this range.

TABLE 10

The dinitrotoluene hydrogenation data for example 4.

| Metric Tons TDA yielded per kilogram of precious metal | Hydrogenation Activity in ml $H_2$ per minute per milligram of precious metal |
|---|---|
| 0.45 | 234 |
| 0.48 | 300 |
| 1.18 | 327 |
| 1.94 | 360 |
| 2.84 | 383 |
| 3.69 | 409 |
| 4.60 | 448 |
| 5.75 | 446 |
| 6.93 | 444 |
| 7.99 | 455 |
| 10.16 | 473 |
| 11.34 | 433 |
| 12.52 | 487 |
| 13.73 | 437 |
| 14.91 | 463 |
| 16.09 | 468 |
| 17.30 | 469 |
| 18.51 | 461 |
| 19.69 | 454 |
| 20.84 | 416 |
| 22.02 | 427 |
| 23.14 | 426 |
| 24.35 | 404 |
| 25.47 | 389 |
| 26.62 | 420 |
| 27.74 | 367 |
| 28.31 | 353 |
| 28.98 | 344 |
| 29.83 | 340 |
| 30.95 | 359 |
| 32.13 | 370 |
| 33.27 | 354 |
| 34.42 | 364 |
| 35.57 | 347 |
| 36.72 | 333 |
| 37.90 | 332 |
| 38.99 | 327 |

EXAMPLE 5

During the last steps of the preparation of a 4.5 wt. % Pd+0.5 wt. % Pt+5.0 wt. % Fe catalyst on a 50% compressed acetylene black made by Degussa's proprietary technology, an activated carbon (steamed activated and based on wood—this is the first type of such a support used here) was added to an aqueous suspension of the catalyst in the ratio of 5 parts activated carbon to 1 part catalyst on a weight basis. This mixture was stirred to homogeneity, filtered and then washed with deionised water. The resulting catalytic mixture had the final metal loading of 0.75 wt. % Pd+0.083 wt. % Pt+0.83 wt. % Fe, contained 13.1 wt. % water and had a filtration time of 2 minutes and 41 seconds (please see Application example 3).

EXAMPLE 6

During the last steps of the preparation of a 4.5 wt. % Pd+0.5 wt. % Pt+5.0 wt. % Fe catalyst on a 50% compressed acetylene black made by Degussa's proprietary technology, activated carbon (steam activated and based on wood—this is the second type of such a support used here) was added to an aqueous suspension of the catalyst in the ratio of 5 parts activated carbon to 1 part catalyst on a weight basis. This catalytic mixture was stirred to homogeneity, filtered and then washed with deionised water. The resulting mixture had the final metal loading of 0.75 wt. % Pd+0.083 wt. % Pt+0.83 wt. % Fe, contained 31.1 wt. % water and had a filtration time of 3 minutes and 08 seconds (please see Application example 3). This catalytic mixture was tested for the pulse hydrogenation of DNT to TDA as according to application example 1. The results for the DNT hydrogenation test can be seen in table 11 and FIG. 3. The maximum DNT hydrogenation activity during this test was 483 ml $H_2$/min/mg of precious metal and the final activity was 303 ml $H_2$/min/mg of precious metal at the yield of 38.8 MT of TDA per kg of precious metal resulting in a deactivation rate of 37.3% over this range.

TABLE 11

The dinitrotoluene hydrogenation data for example 6.

| Metric Tons TDA yielded per kilogram of precious metal | Hydrogenation Activity in ml $H_2$ per minute per milligram of precious metal |
|---|---|
| 0.9 | 275 |
| 1.7 | 312 |
| 2.5 | 364 |
| 3.5 | 396 |
| 4.1 | 362 |
| 5.1 | 417 |
| 6.1 | 430 |
| 7.0 | 400 |
| 7.6 | 381 |
| 8.9 | 413 |
| 9.9 | 467 |
| 11.0 | 483 |
| 12.0 | 449 |
| 13.2 | 447 |
| 14.0 | 412 |
| 15.1 | 483 |
| 16.2 | 483 |
| 17.3 | 433 |
| 18.3 | 432 |
| 19.3 | 426 |
| 19.9 | 409 |
| 20.9 | 395 |
| 22.0 | 409 |
| 22.9 | 349 |
| 24.0 | 398 |
| 24.9 | 328 |
| 25.9 | 354 |
| 27.0 | 349 |
| 28.0 | 332 |
| 29.1 | 343 |
| 30.2 | 350 |
| 31.2 | 346 |
| 32.3 | 335 |
| 33.4 | 335 |
| 34.5 | 321 |
| 35.5 | 302 |
| 36.7 | 309 |
| 37.8 | 302 |
| 38.8 | 303 |

EXAMPLE 7

During the last steps of the preparation of a 4.5 wt. % Pd+0.5 wt. % Pt+5.0 wt. % Fe catalyst on a 50% compressed acetylene black made by Degussa's proprietary technology, activated carbon (steam activated and based on wood—this is the second type of such a support used here) was added to an aqueous suspension of the catalyst in the ratio of 5 parts activated carbon to 1 part catalyst on a weight basis. This mixture was stirred to homogeneity, filtered and then washed with deionised water. The resulting catalytic mixture had the final metal loading of 0.75 wt. % Pd+0.083 wt. % Pt+0.83 wt. % Fe, contained 66 wt. % water and was tested for the pulse hydrogenation of DNT to TDA as according to application example 1. The results for the DNT hydrogenation test can be seen in table 12 and FIG. 3. The maximum DNT hydrogenation activity during this test was 497 ml $H_2$/min/mg of precious metal and the final activity was 319 ml $H_2$/min/mg of precious metal at the yield of ~39.3 MT of TDA per kg of precious metal resulting in a deactivation rate of 37.3% over this range.

TABLE 12

The dinitrotoluene hydrogenation data for example 7.

| Metric Tons TDA yielded per kilogram of precious metal | Hydrogenation Activity in ml $H_2$ per minute per milligram of precious metal |
|---|---|
| 1.1 | 442 |
| 2.0 | 376 |
| 2.9 | 392 |
| 4.0 | 437 |
| 5.1 | 424 |
| 6.2 | 396 |
| 7.3 | 453 |
| 8.4 | 436 |
| 9.6 | 477 |
| 10.7 | 453 |
| 11.8 | 460 |
| 13.0 | 497 |
| 14.1 | 443 |
| 15.2 | 486 |
| 16.4 | 477 |
| 17.5 | 465 |
| 18.7 | 462 |
| 19.8 | 468 |
| 21.0 | 463 |
| 22.1 | 458 |
| 23.3 | 465 |
| 24.4 | 465 |
| 25.6 | 455 |
| 26.7 | 440 |
| 27.9 | 422 |
| 29.0 | 454 |
| 30.2 | 433 |
| 31.3 | 431 |
| 32.5 | 409 |
| 33.6 | 409 |
| 34.7 | 402 |
| 35.9 | 367 |
| 37.0 | 370 |
| 38.2 | 341 |
| 39.3 | 319 |

EXAMPLE 8

During the last steps of the preparation of a 4.5 wt. % Pd+0.5 wt. % Pt+5.0 wt. % Fe catalyst on a 100% compressed acetylene black made by Degussa's proprietary technology, sibunit powder (this sibunit powder was described in comparative example 2) was added to an aqueous suspension of the catalyst in the ratio of 5 parts sibunit powder to 1 part catalyst on a weight basis. This mixture was stirred to homogeneity, filtered and then washed with deionised water. The resulting catalytic mixture had the final metal loading of 0.75 wt. % Pd+0.083 wt. % Pt+0.83 wt. % Fe and it was tested for the pulse hydrogenation of DNT to TDA as according to application example 1. The results for the DNT hydrogenation test can be seen in table 13 and FIG. 3. The maximum DNT hydrogenation activity during this test was 439 ml $H_2$/min/mg of precious metal and the final activity was 312 ml $H_2$/min/mg of precious metal at the yield of 37.1 MT of TDA per kg of precious metal resulting in a deactivation rate of 28.9% over this range.

TABLE 13

The dinitrotoluene hydrogenation data for example 8.

| Metric Tons TDA yielded per kilogram of precious metal | Hydrogenation Activity in ml $H_2$ per minute per milligram of precious metal |
|---|---|
| 0.7 | 274 |
| 1.4 | 302 |
| 1.9 | 279 |
| 2.8 | 347 |
| 3.7 | 411 |
| 4.7 | 388 |
| 5.8 | 402 |
| 6.9 | 398 |
| 8.0 | 407 |
| 9.1 | 435 |
| 10.2 | 419 |
| 11.3 | 419 |
| 12.4 | 439 |
| 13.6 | 409 |
| 14.7 | 407 |
| 15.9 | 416 |
| 17.0 | 404 |
| 18.1 | 416 |
| 19.2 | 416 |
| 20.4 | 404 |
| 21.5 | 413 |
| 22.7 | 378 |
| 23.8 | 366 |
| 24.9 | 372 |
| 26.0 | 373 |
| 27.0 | 346 |
| 28.0 | 365 |
| 29.1 | 348 |
| 30.2 | 350 |
| 31.4 | 336 |
| 32.5 | 340 |
| 33.6 | 341 |
| 34.8 | 333 |
| 35.9 | 335 |
| 37.1 | 312 |

EXAMPLE 9

During the last steps of the preparation of a 4.5 wt. % Pd+0.5 wt. % Pt+5.0 wt. % Fe catalyst on a 100% compressed acetylene black made by Degussa's proprietary technology, sibunit powder (this sibunit powder was described in comparative example 2) was added to an aqueous suspension of the catalyst in the ratio of 5 parts sibunit powder to 1 part catalyst on a weight basis. This catalytic mixture was stirred to homogeneity, filtered and then washed with deionised water. The resulting mixture had the final metal loading of 0.75 wt. % Pd+0.083 wt. % Pt+0.83 wt. % Fe, contained 49.3 wt. % water and had a filtration time of 3 minutes and 43 seconds (please see Application example 3).

EXAMPLE 10

During the last steps of the preparation of a 4.5 wt. % Pd+0.5 wt. % Pt+5.0 wt. % Fe catalyst on a 100% compressed acetylene black made by Degussa's proprietary technology, activated carbon (steam activated and based on wood—this is the second type of such a support used here) was added to an aqueous suspension of the catalyst in the ratio of 5 parts activated carbon to 1 part catalyst on a weight basis. This catalytic mixture was stirred to homogeneity, filtered and then washed with deionised water. The resulting mixture had the final metal loading of 0.75 wt. % Pd+0.083 wt. % Pt+0.83 wt. % Fe, contained 64.6 wt. % water and had a filtration time of 2 minutes and 18 seconds (please see Application example 3).

EXAMPLE 11

During the last steps of the preparation of a 4.5 wt. % Pd+0.5 wt. % Pt+5.0 wt. % Fe catalyst on an steam activated wood based carbon (type 1) made by Degussa's proprietary technology, sibunit powder (this sibunit powder was described in comparative example 2) was added to an aqueous suspension of the catalyst in the ratio of 5 parts sibunit powder to 1 part catalyst on a weight basis. This catalytic mixture was stirred to homogeneity, filtered and then washed with deionised water. The resulting mixture had the final metal loading of 0.75 wt. % Pd+0.083 wt. % Pt+0.83 wt. % Fe, contained 3.0 wt. % water and had a filtration time of 0 minutes and 38 seconds (please see Application example 3).

Table 14 summarizes the data measured on the catalysts, supports, reaction aids and catalytic mixtures described here. One can see that the addition of a reaction aid not only improves the filterability of the catalyst system, but is also improves the activity of the catalysts on a active metal basis. In any case, neither the activity nor the selectivity of the catalyst is made worse by the addition of the reaction aid. Another advantage was that one could more readily control the final amount of water in the catalyst from either very high levels of ~80 wt. % to practically 0 wt. % depending of the desired properties of the catalyst.

TABLE 14

The summary of the catalyst data

| Cat[1] | Sup.[2] | Rxn Add[3] | Cat. to Add. Ratio[4] | wt. % $H_2O$ | CA Act.[5] | DNT max Act.[6] | DNT final act.[7] | Final TDA Yield[8] | % Deact. DNT test[9] | Filter Time in m & s[10] |
|---|---|---|---|---|---|---|---|---|---|---|
| CE1 | AB 50% | — | — | <1 | — | — | — | — | — | 5 m 15 s |
| CE2 | Sib | — | — | <1 | — | — | — | — | — | 0 m 41 s |
| CE3 | AB 50% | — | 1:5 AB 50% | 74 | 8043 | 429 | 236 | 39.9 | 45 | 4 m 39 s |
| CE4 | AB 50% | — | — | 81 | 4440 | 367 | 219 | 40 | 40.3 | >8 m |
| CE5 | AB 50% | — | 1:5 AB 50% | 78 | — | — | — | — | — | 4 m 28 s |
| CE6 | AB 100% | — | — | 78 | 3920 | — | — | — | — | >8 m |
| CE7 | AC | — | — | — | — | 216 | 173 | 24 | 19.9 | — |
| CE8 | Sib | — | — | 27 | 1700 | Activity was too low to measure | | | | 0 m 35 s |
| E1 | AB 50% | Sib | 1:5 | 1 | 10324 | 632 | 510 | 40 | 19.3 | 2 m 03 s |
| E2 | AB 100% | Sib | 1:5 | 30 | 11525 | 418 | 297 | 39.9 | 28.9 | 2 m 15 s |
| E3 | AB 100% | Sib | 1:5 | 36 | — | 407 | 295 | 38.7 | 27.5 | 2 m 24 s |
| E4 | AB 50% | Sib | 1:5 | 58 | 9124 | 487 | 327 | 39 | 32.9 | — |
| E5 | AB 50% | 1-AC[11] | 1:5 | 13 | — | — | — | — | — | 2 m 41 s |
| E6 | AB 50% | 2-AC[12] | 1:5 | 31 | — | 483 | 303 | 38.8 | 37.3 | 3 m 08 s |
| E7 | AB 50% | 2-AC | 1:5 | 66 | — | 497 | 319 | 39.3 | 39.3 | — |
| E8 | AB 100% | Sib | 1:5 | — | — | 439 | 312 | 37.1 | 28.9 | — |
| E9 | AB 100% | Sib | 1:5 | 49 | — | — | — | — | — | 3 m 43 s |
| E10 | AB 100% | 2-AC | 1:5 | 65 | — | — | — | — | — | 2 m 18 s |
| E11 | 1-AC | Sib | 1:5 | 30 | — | — | — | — | — | 0 m 38 s |

[1]Catalyst designation in patent: CE = comparative example and E = example.

[2]Sup. = Support type: AB = Acetylene Black with % compression, AC = activated carbon (with type number) and Sib = sibunit powder.

[3]Reaction aid: AC = activated carbon (with type number) and Sib = sibunit powder.

[4]The catalyst to additive ratio on a weight basis, where the additive is either fresh support or a reaction aid.

[5]The cinnamic acid hydrogenation activity in ml $H_2$/min/milligram of precious metal.

[6]The maximum activity of the DNT pulse hydrogenation test in the units of ml $H_2$/min/mg precious metal.

[7]The final activity of the DNT pulse hydrogenation test in the units of ml $H_2$/min/mg precious metal.

[8]The final TDA yield during the DNT test in units of MT TDA/kg precious metal.

[9]The % of deactivation during the DNT pulse hydrogenation test to the final yield.

[10]The filtration time as determined by the filtration test in minutes (m) and seconds (s).

[11]1-AC = Activated carbon type 1.

[12]1-AC = Activated carbon type 2.

Figure 3:
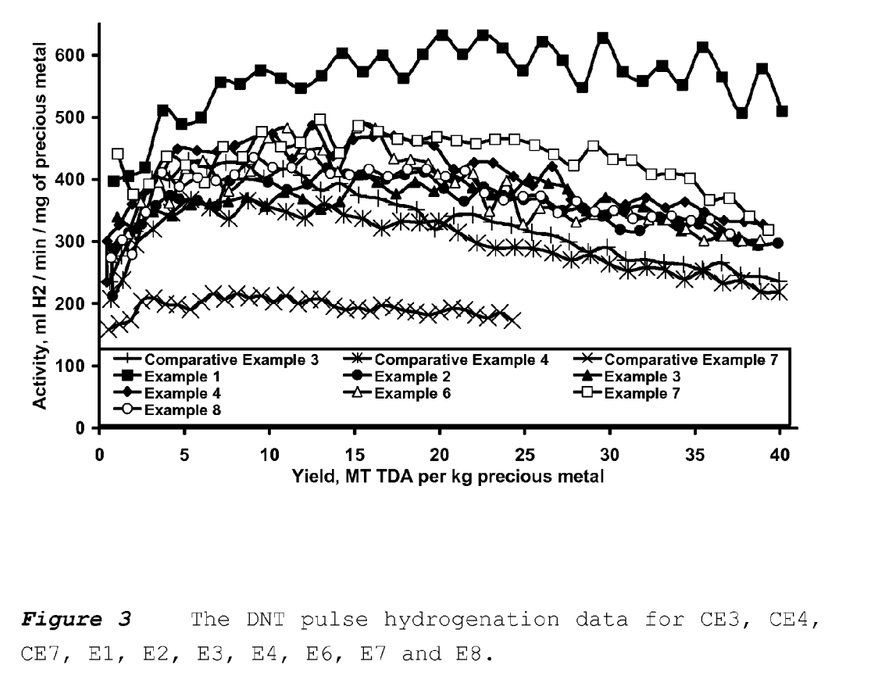
FIG. 3 is a graph showing DNT pulse hydrogenation data for various catalyst compositions.

The DNT hydrogenation results (see application example 1) are graphically demonstrated in FIG. 3.

While modifications may be made by those skilled in the art, such modifications are encompassed within the spirit of the present invention as defined by these disclosures and claims.

The invention claimed is:

1. A catalytic mixture comprising:
   a) a metal powder catalyst comprising metal crystals that have been fixed to a powder support by a fixing agent; and
   b) a reaction aid which aids in filtering but does not interfere with a reaction, which comprises particles with a particle size distribution, $D_{50}$, of 5 μm-1000 μm and which is selected from the group consisting of a sibunit powder and an activated carbon;
   wherein the ratio of said reaction aid to said catalyst is 0.05-20 on a weight basis.

2. The catalytic mixture of claim 1, wherein the ratio of reaction aid to catalyst is from 4 to 6 on a weight basis.

3. The catalytic mixture of claim 1, wherein the ratio of reaction aid to catalyst is 5 on a weight basis.

4. The catalytic mixture of claim 1, comprising an acetylene black supported precious metal catalyst and sibunit powder, wherein the ratio of sibunit powder to catalyst is from 0.05 to 20 on a weight basis.

5. The catalytic mixture of claim 4, wherein the ratio of sibunit powder to catalyst is 5 on a weight basis.

6. The catalytic mixture of claim 1, comprising an acetylene black supported precious metal catalyst and activated carbon, wherein the ratio of said activated carbon to catalyst is from 0.3 to 20 on a weight basis.

7. The catalytic mixture of claim 6, wherein the ratio of activated carbon to catalyst is from 4.0 to 6.0 on a weight basis.

8. The catalytic mixture of claim 7, wherein the ratio of activated carbon to catalyst is 5 on a weight basis.

9. The catalytic mixture of claim 1, comprising an activated carbon derived from one or more sources selected from the group consisting of wood, peat, coal, saw dust, carbon containing waste materials, rice husks, coconut shells, bones, lignite, petroleum based residues and sugars.

10. The catalytic mixture of claim 9, further comprising a metal selected from the group consisting of: Pt or Fe.

11. The catalytic mixture of claim 9, further comprising Pd.

12. The catalytic mixture of claim 11, further comprising acetylene black.

13. In a chemical reaction in which an organic compound or a nitrate undergoes a hydrogenation, dehydrogenation, isomerization, reductive amination, reductive alkylation, oxidation and/or hydration, the improvement comprising catalyzing said reaction with the catalytic mixture of claim 1.

14. The improvement of claim 13, wherein said chemical reaction is the hydrogenation of an olefin.

15. The improvement of claim 13, wherein said chemical reaction is the hydrogenation of a nitro compound.

16. The improvement of claim 13, wherein said chemical reaction is the hydrogenation of an aromatic nitro compound.

17. The improvement of claim 13, wherein said chemical reaction is the hydrogenation of dinitrotoluene to toluenediamine.

18. The improvement of claim 17, wherein said catalytic mixture comprises a precious metal powder catalyst containing Pd, Pt and Fe.

19. The improvement of claim 18, wherein said Pd, Pt and Fe are present in said precious metal powder catalyst at the weight ratios of 9:1:10 for Pd:Pt:Fe.

20. The improvement of claim 19, wherein the reaction aid in said catalytic mixture comprises sibunit powder.

* * * * *